(12) United States Patent
Strauss et al.

(10) Patent No.: US 10,932,694 B2
(45) Date of Patent: Mar. 2, 2021

(54) DEVICE FOR DETECTING PRESENCE AND SEVERITY OF EDEMA

(71) Applicant: CARDIMETRIX LLC, Teaneck, NJ (US)

(72) Inventors: Benjamin Strauss, Teaneck, NJ (US); Eric Forkosh, Woodmere, NY (US); Kalman Katlowitz, New York, NY (US); Lawrence Baruch, New York, NY (US)

(73) Assignee: CARDIMETRIX LLC

( * ) Notice: Subject to any disclaimer, the term of this patent is extended or adjusted under 35 U.S.C. 154(b) by 706 days.

(21) Appl. No.: 14/801,960

(22) Filed: Jul. 17, 2015

(65) Prior Publication Data

US 2016/0015297 A1   Jan. 21, 2016

Related U.S. Application Data

(60) Provisional application No. 62/025,636, filed on Jul. 17, 2014.

(51) Int. Cl.
*A61B 5/107*   (2006.01)
*A61B 5/00*   (2006.01)

(52) U.S. Cl.
CPC .......... *A61B 5/1073* (2013.01); *A61B 5/4878* (2013.01); *A61B 5/0004* (2013.01); *A61B 5/1075* (2013.01); *A61B 5/4848* (2013.01); *A61B 5/6828* (2013.01)

(58) Field of Classification Search
None
See application file for complete search history.

(56) References Cited

U.S. PATENT DOCUMENTS

| 4,085,746 | A | * | 4/1978 | Castiglia | A61F 13/066 128/DIG. 15 |
|---|---|---|---|---|---|
| 4,566,461 | A | * | 1/1986 | Lubell | A61B 5/024 377/24.2 |
| 7,201,726 | B2 | * | 4/2007 | Vastano | A61B 5/1073 600/587 |
| 2011/0098549 | A1 | | 4/2011 | Hayim et al. | |
| 2012/0179067 | A1 | | 7/2012 | Wekell | |
| 2014/0088461 | A1 | * | 3/2014 | Mack | A43D 1/025 600/595 |

FOREIGN PATENT DOCUMENTS

WO   2009/125327 A1   10/2009

OTHER PUBLICATIONS

Notification of Transmittal of the International Search Report and the Written Opinion of the International Search Authority, or the Declaration for International Patent Application No. PCT/US/15/40836, dated Oct. 23, 2015.
International Search Report for International Application No. PCT/US/15/40836, dated Oct. 23, 2015.

* cited by examiner

*Primary Examiner* — Matthew Kremer
(74) *Attorney, Agent, or Firm* — Barnes & Thornburg LLP (57) ABSTRACT

A device monitors circumferences of the leg, and estimates volume of a section of the leg, to detect edema, which can be indicative of CHF, and gauge the effectiveness of medication. The device sends the calculations to a database via BLUETOOTH™ for the patient's treating medical personnel to see.

25 Claims, 5 Drawing Sheets

DEVICE FOR DETECTING PRESENCE AND SEVERITY OF EDEMA

RELATED APPLICATIONS

The present application is related to and claims priority to U.S. Provisional Patent Application Ser. No. 62/025,636, filed on Jul. 17, 2014. The subject matter disclosed in that provisional application is hereby expressly incorporated into the present application in its entirety.

FIELD

The present invention is in the field of electronic measurement of anatomical areas. More particularly, the present invention is in the field of measuring monitoring edema.

BACKGROUND

Congestive Heart Failure (CHF) is a condition in which the heart does not sufficiently pump blood to and from the organs of the body. The American Heart Association estimates that there are approximately five million Americans living with CHF, and there are approximately 53,000 deaths due to CHF each year, making it one of the most significant public health burdens in the United States. As blood is pumped progressively less effectively due to CHF, fluid can aggregate in the peripherally, in the extremities, causing edema, also known as swelling. As peripheral edema increases, so does the volume of the leg. To treat the symptoms of swelling, medications that cause the body to excrete more fluid, and thus reduce the buildup of fluid and subsequent swelling, can be administered. The effectiveness of the medication can be gauged, and its dosages adjusted, by regular monitoring of the volume of the leg.

Monitoring for the presence of CHF and quantification of fluid retention in the peripheral extremities is currently accomplished by cumbersome methods. One such method involves wrapping a tape measure around the same part of the leg one or more times per day and measuring the circumference, noting any changes, and reporting the results to the patient's treating doctor. As the volume of a section of the leg increases, there is a proportional increase in the area and circumference of a circle circumscribed around it. Because circumference is linearly proportional to length, the change in length is linearly proportional to the change in circumference. Thus, the change in volume can be estimated by monitoring the change in length of circumscription around a particular location of the leg. Compliance with this method can be low, and obtained results can be inaccurate. Another method of monitoring leg volume is accomplished by filling a bucket with water, and having the patient place his leg in the bucket. The volume of water displaced is equal to the volume of the leg. This volume is measured, and the results are reported to the patient's treating doctor. Again, the cumbersome nature of this method can cause low patient compliance in monitoring leg volume, and can also lead to inaccurate results. Thus, there exists deficiency in the current monitoring methods.

SUMMARY

Thus, conventional equipment is cumbersome, can be challenging to comply with, and are conducive to inaccurate measurements. Further, there exists no device or system for the automated calculation of circumference of the leg, and estimation of leg volume. The above problems, as well as other problems which include patient compliance, may be solved by various aspects of the disclosed embodiment of a device for detecting presence and severity of edema.

Disclosed embodiments may implement an electronic method of calculating circumference the foot and part of the leg, and estimating volume of the foot and part of the leg. When the device, which fits around the leg like a sock, may be worn by the patient, it automatically measures the circumference reading at multiple points. The results may be sent via BLUETOOTH™ to a device that can relay the transmission to a database for the patient's treating doctor to monitor. In another version of this device and implementation, the circumferences obtained may be used to generate a three-dimensional model of the foot and leg, and in conjunction with parameters based on basic patient information, an estimate for the volume may be generated.

Additional features of the present disclosure will become apparent to those skilled in the art upon consideration of illustrative embodiments exemplifying the best mode of carrying out the disclosure as presently perceived.

DETAILED DESCRIPTION

Figure 1A:
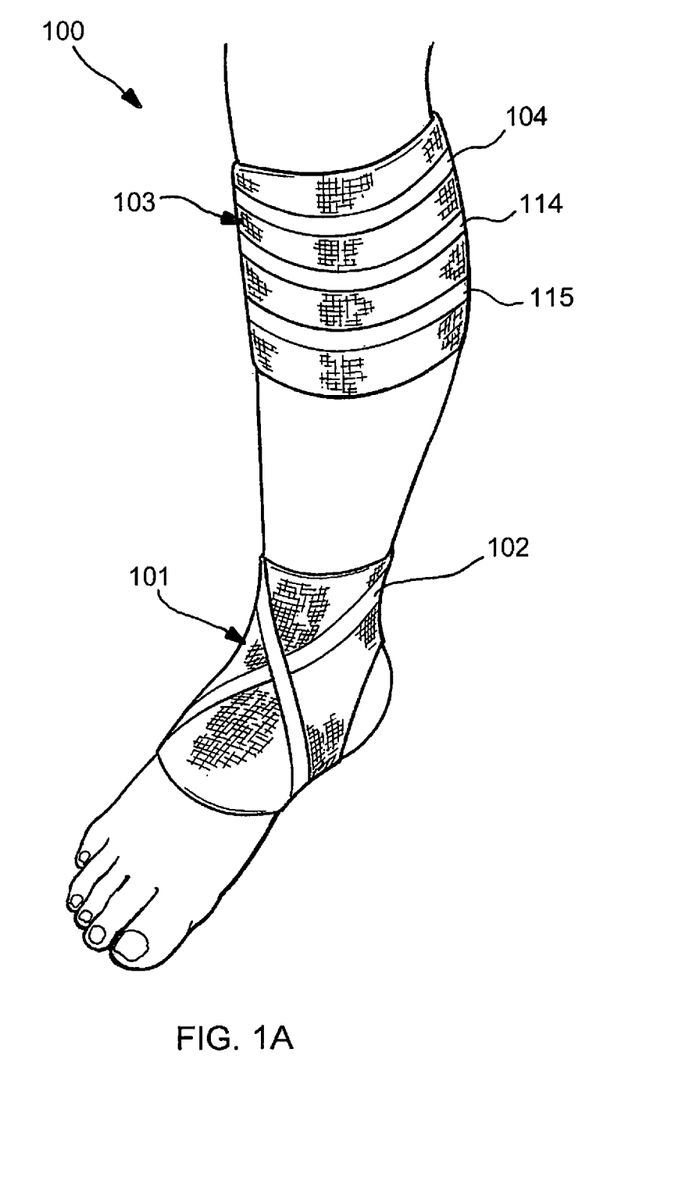
FIG. 1A is a front view of the brace that may be worn around the leg.
Figure 1B:
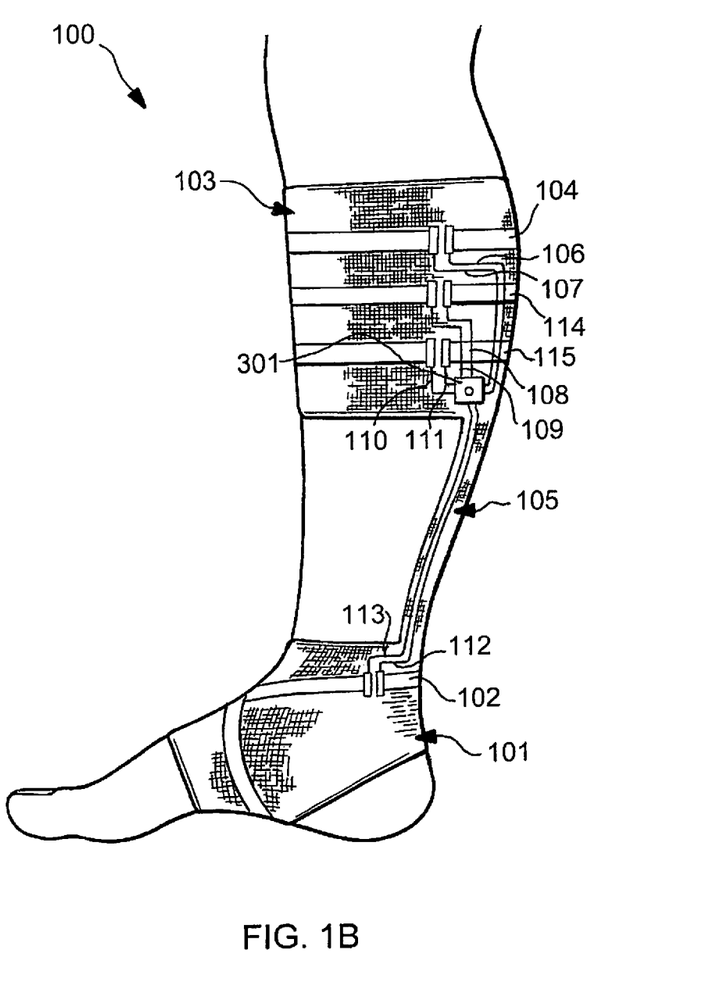
FIG. 1B is a side view of the brace that may be worn around the leg.

FIG. 1A and FIG. 1B show one embodiment of the disclosed invention wherein a stretchable material may be worn like a brace 100 and include a foot portion 101 and an leg portion that may be worn on a user's leg. The brace foot portion 101 and the brace leg portion 103 may be connected by a common piece of fabric 105 that may be positioned on the back of the user's leg. In some embodiments, the brace 100 may be a sock worn on the foot.

There may be three or more stretchable wires whose electrical resistance increases in linear proportion with length 104, 114, 115 that form circumferences around the brace leg portion 103, and may be sewn into it. Connective wires 106, 107 may be connected to each end of the top stretchable wire 104, and both connective wires 106, 107 may be connected to two poles of one of a voltmeter (not shown) included in the signal acquisition and transmission hardware 301 (as illustrated in FIG. 1B). Connective wires 108, 109 may be connected to each end of the middle stretchable wire 114; both connective wires 108, 109 may be connected to two poles of the voltmeter (not shown) in the signal acquisition and transmission hardware 301. Connective wires 110, 111 may be connected to each end of the bottom stretchable wire 115; both connective wires 110, 111 may be connected to two poles of the voltmeter (not shown) in the signal acquisition and transmission hardware 301. Similarly, in the foot brace 101, stretchable wire whose electrical resistance changes in linear proportion to length 102 may be sewn into the brace, forming a figure eight, e.g., wherein two circumferences around the foot brace. The wire 102 crosses over itself at the top of the foot brace.

Figure 2:
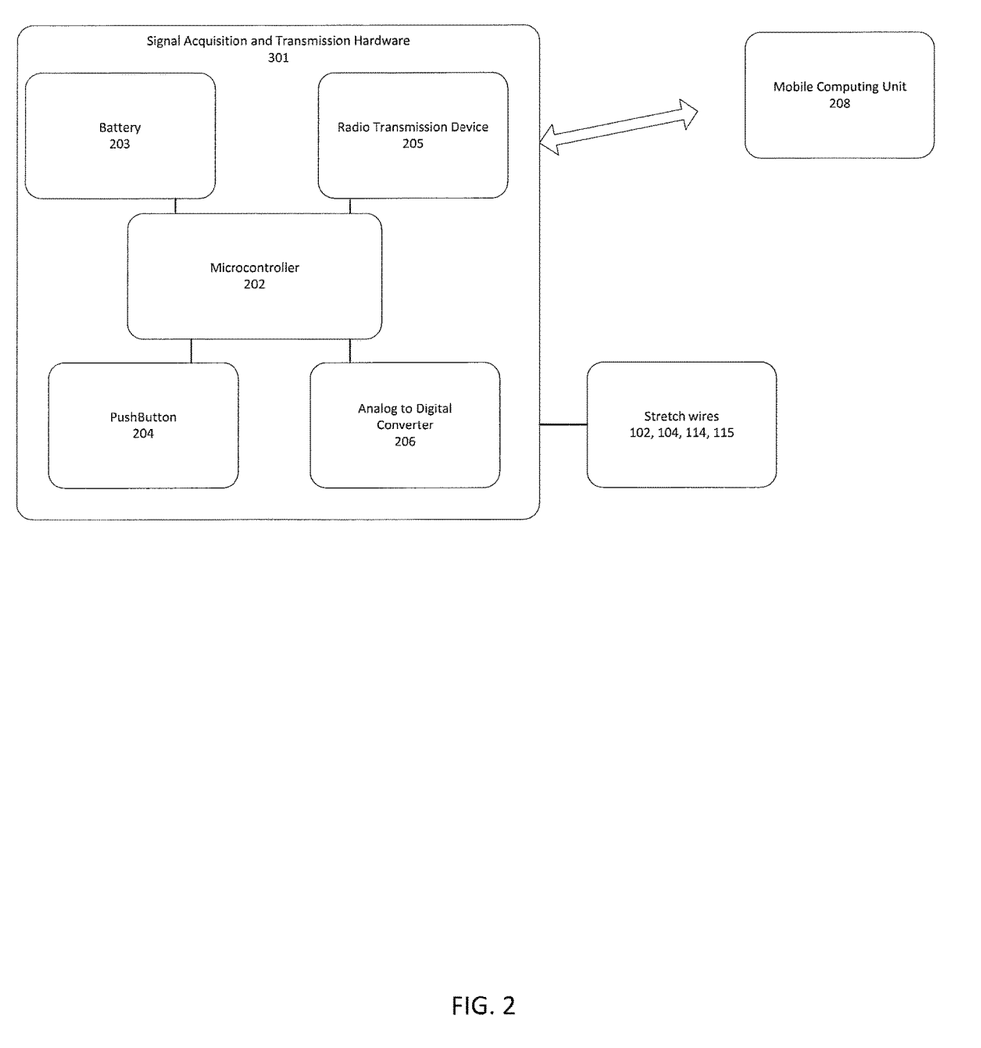
FIG. 2 is a block diagram of the signal acquisition and transmission hardware in combination with a mobile computing unit for displaying the circumferences calculated.

As illustrated in FIG. 2, signal and transmission hardware 301 may include a coin cell battery 203 coupled to other components illustrated therein to provide power to the signal acquisition and transmission hardware 301. A push button 204 on the signal acquisition and transmission hardware 301 may be depressed to power components included in the brace 100. Microcontroller 202 may be in communication with the push button 204, battery 203, an analog to digital converter 206, and a radio transmission device 205.

Further, microcontroller 202 may be connected to the coin cell battery 203 or another power source (not shown) to provide a current fed through the wires 102, 104, 114, 115 to determine a resistance indicative of lengths of wire in the brace (as explained in detail below). Thus, it should be understood that the current fed through the wires 102, 104, 114, 115 may be injected on a limited basis when the brace 100 is operable to determine the resistance indicative of those lengths. Thus, when the microcontroller 202 receives a signal from the pushbutton 204 to acquire signals across the stretchable wires, 102, 104, 114, 115, an electrical current of known value may be passed through each of the stretchable wires 102, 104, 114, 115.

As a result, a voltage exists in each stretchable wires 102, 104, 114, 115 because of the current being passed through the stretchable wires. The resulting analog voltage value may be optionally stored and also converted by an analog-to-digital converter 206 and then may be input to the microcontroller 202. The voltage of each of the wires 102, 104, 114, 115 may be one or more voltmeters in the microcontroller 202 (e.g., an implementation including a single voltmeter may measure the voltages sequentially, whereas an implementation with a plurality of voltmeters may measure the voltages simultaneously).

In some embodiments, microcontroller 202 may include a processor and memory with instructions, that when executed cause the processor to calculate circumferences for the stretchable wires and corresponding volumes as described with respect to FIGS. 4-5 below.

As seen in FIG. 2, the brace foot portion 103 of FIGS. 1A-1B may be in wireless communications with a mobile computing unit 208 for displaying and transmitting data received from the microcontroller. All calculated circumference and volume values may be transmitted via a BLUETOOTH™ radio 205 connection to a mobile computing unit 208, which can be a smartphone or a dedicated device. The mobile computing unit can transmit the results via internet connection to the treating medical personnel.

Figure 3:
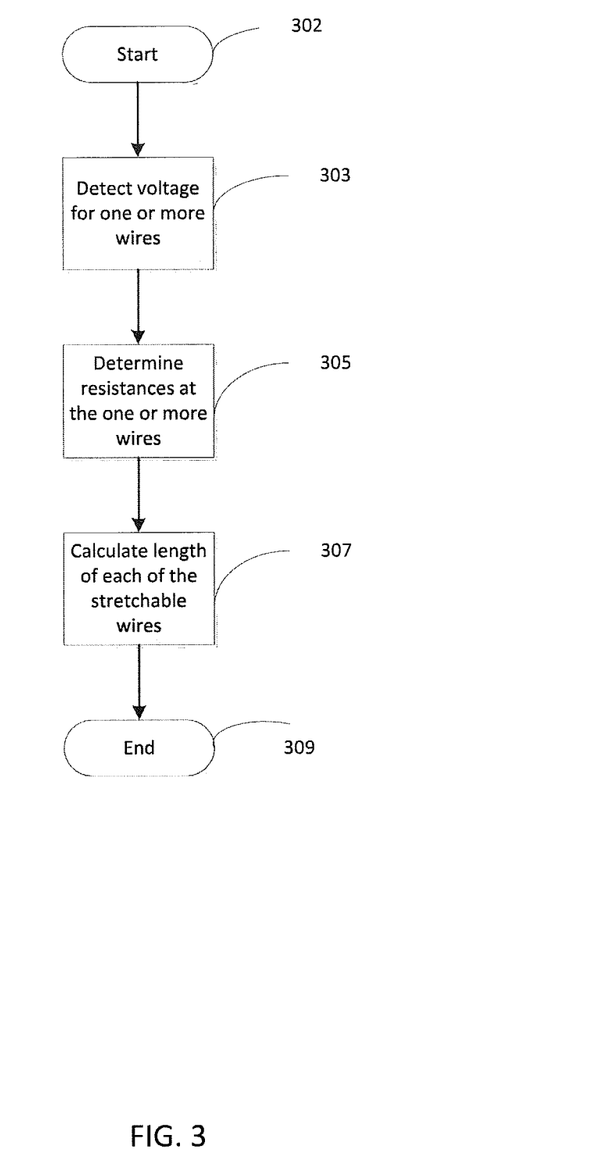
FIG. 3 is a diagram of the process to calculate circumference.

As seen in FIG. 3, the device can be configured to execute a process that is based on Ohm's Law. Thus, the process being at 301 and control proceeds to 303 at which a voltage is detected for one or more of the wires 102, 104, 114, 115. Control then proceeds to 305, at which the resistance appearing on the respective wire is determined since the injected current and detected voltage are known. Ohm's Law dictates that Voltage, V, is equal to current, i, multiplied by resistance, R, i.e., V=iR.

Furthermore, it is known that the resistance of a wire increases in linear proportion to the increase in length of the wire. Thus, for example, with reference to wires 102, 104, 114, 115, each wire's resistance may be 350 Mega Ohms per inch. Thus, theoretically, if the length of one of these wire increases by one inch, the total resistance of that wire will increase by 350 Mega Ohms as well (which may be referred to as a "stretch constant").

Likewise, if the length of that wire increases by two inches, the total resistance of the wire will increase by 700 Mega Ohms. Accordingly, if a change in voltage increases by 350 Mega Ohms, the resistance determined will be indicative of a baseline resistance output (corresponding to an unstretched circumference of the wiring) plus one inch.

Accordingly, at 307, the total length of the stretchable wire(s) is determined and used to determine the total volume of the leg on which the brace 100 is attached. The method cads 309. This data may be output from the microcontroller, e.g., transmitted via to a mobile computing unit for subsequent display and use.

In other words, because a wire has an intrinsic property of resistance per length, $R_1/l$, the microcontroller and disclosed inventive process can use resistance R of one of the stretchable wires, 102, 104, 114, 115, and equate it to resistance per length, $R_1/l$, a known value, multiplied by total length of the wire. Thus, resistance per length multiplied by total length of the wire may be used to represent the total resistance in Ohm's Law. The only unknown variable may be total length of the wire, which represents the circumference. This variable can be isolated and solved for. The device computes this value from each of the wires 102, 104, 114, 115.

Figure 4:
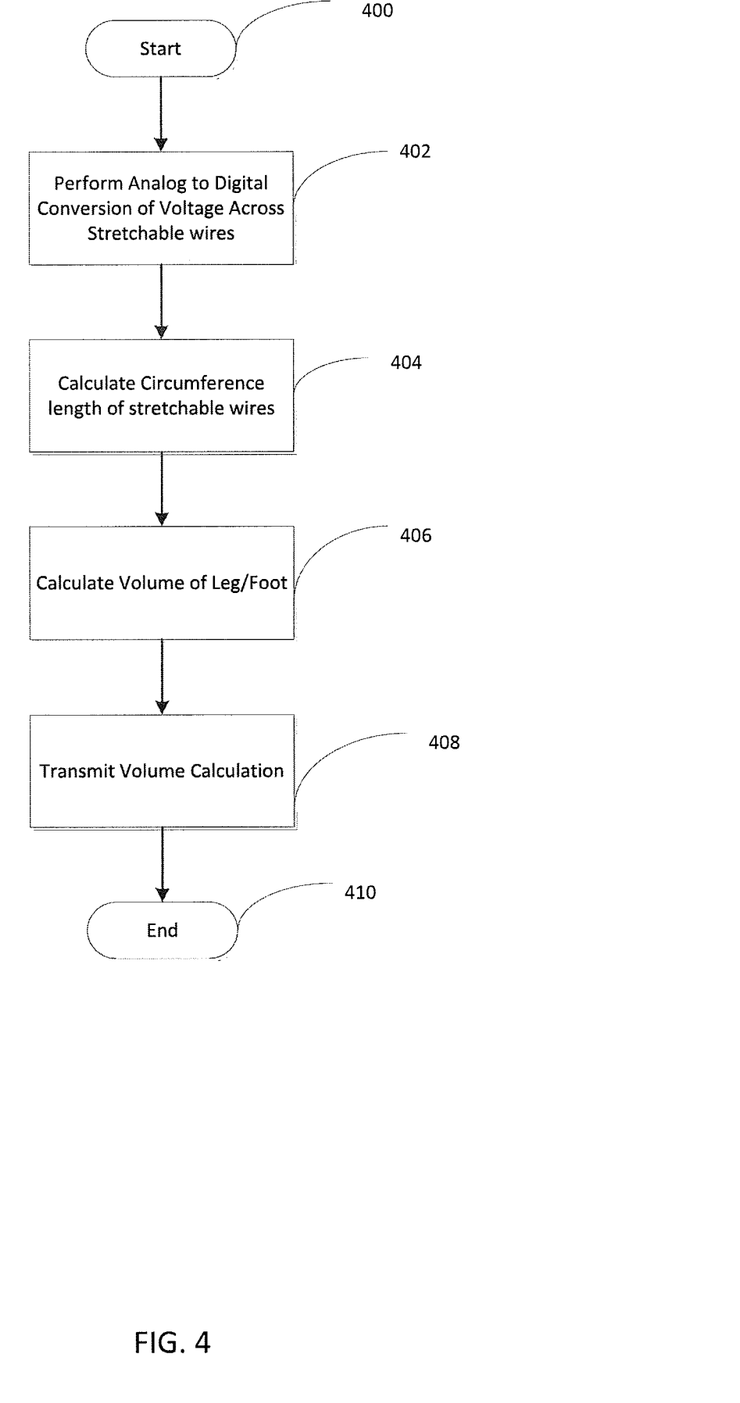
FIG. 4 is a flowchart of a process of determining a volume of a foot.

FIG. 4 shows one implementation of a process to approximate the volume for user's leg under direction of a microcontroller starting at 400. First, analog to digital conversion of voltage measured across a plurality of stretchable wires is performed at 402. Control then proceeds to 404, at which the circumferential length of the stretchable wire is calculated for each wire as described in detail in relation to FIG. 3. Control then proceeds to 406, at which a volume of the leg may be calculated using the calculated circumferences. As mentioned above, the volume of the leg may include the lower leg portion and/or ankle portion of the leg.

Control then proceeds to 408 at which the calculated volume can be transmitted to a user and/or a remote caregiver and communicated to the user via visual and/or audible communications (e.g., on a user's mobile computing unit). The process ends at 410.

In further detail, the approximate volume of the leg may be calculated by approximating the upper leg is as a cylinder. Thus, the distance (e.g., height) between each the wires for which circumference has been calculated may be constant and known. For example, the distance between the bottom wire 115 and the middle wire 114 (illustrated in FIGS. 1A and 1B) may be denoted "A." The distance between the middle wire 114 and the top wire 104 (illustrated in FIGS. 1A and 1B) may be denoted as "B." The distance between the top wire 104 and the top of the brace 103 on the upper leg 103 is also known. This distance is called "C."

In this example, the volume of the section of the leg covered by the brace on the upper leg may be approximated as the sum of three cylinders. It is the sum of the cylinder contained between the lowest wire 115 and the middle wire 114; the cylinder contained between the middle wire 114 and the upper wire 104; and the cylinder contained between the upper wire 114 and the top of the brace 103. The circumference attained by the bottom wire 115 is called "D." The circumference attained by the middle wire 114 is called "E." The circumference attained by the top wire 104 is called "F." Mathematically, the volume approximation is represented as $$\text{Volume} = \frac{D^2}{4\pi}A + \frac{E^2}{4\pi}B + \frac{F^2}{4\pi}C.$$

The ankle volume can also be calculated along with the leg volume using the ankle's circumference (for example, circumference of the "figure eight" shape of wire in FIG.

1B). A conversion factor to convert from figure eight circumference to volume can be provided. This conversion factor can be established before regular use of the device by comparing the figure eight circumference with ankle volume obtained with a water displacement method. The relationship between the circumference and the square root of the volume is linear. This factor can be multiplied the circumference of the figure eight obtained with regular use, to obtain volume of the ankle.

This brace 100 may be utilized, for example, by a heart failure patient who is discharged from the hospital. Heart failure patients are most frequently discharged from the hospital when diuresis has been performed on them, and they have been ridden of all the extraneous fluid that usually causes peripheral edema. Thus, when a patient uses the device immediately after their edema has been eliminated, those values attained represent the baseline, or ideal volume. The results from use of the device each day can be transmitted to a remote server, where they can be compared to the baseline and trended. A trend towards an increase from the baseline is indicative of fluid retention and edema in the legs. This data can be used to guide remote titration of oral diuretics—that is, to enable care providers to suggest that patients increase the dosage of diuretics they take on a given day, to return leg volume to baseline.

This sock can be used in conjunction with daily weight measurement to increase sensitivity of fluid retention monitoring. If a patient has gained 1 kilogram of weight, and the results of the device show a gain of 1 liter of volume (combined in both feet), it can be confirmed that all weight that has been gained is due exclusively to fluid retention, and not other causes of weight gain. Conversely, if a patient has gained weight, but shows no increase in volume of the legs, or shows a decrease in volume of the legs, it can be concluded that the patient's weight gain is not due to fluid retention or edema.

It should further be understood that there may utility in a user wearing only a single brace on a leg to provide a representational detection and determination of bilateral edema (e.g., in both legs). Alternatively, a brace may be worn on each leg to be able to detect unilateral, sudden onset edema that may be indicative of a blood clot in the leg (i.e., a deep vein thrombosis or DVT). It should further be understood that calculations and processing described may take place at the microcontroller on the brace and/or at a remote server or remote processing device in communications with the transmission hardware on the brace.

Disclosed embodiments solve a technical problem in the conventional art in that there is no conventional device that is able to measure the volume of a body part, e.g., a human leg, in a user friendly manner so as to provide up to date monitoring data indicative of edema in the user.

The presently disclosed embodiment does this in an unobtrusive compact way that enables the user to maneuver and go about daily activity while still wearing the device. Thus, it should be understood that, in at least one embodiment the user may wear footwear while wearing the brace. In this way, the disclosed embodiments improve the likelihood that a user will adhere to and favorably respond to such monitoring.

Thus, it should be understood that the disclosed invention contemplates a wearable device measuring changes in a body part volume, wherein the wearable device comprises a plurality of sensors that each output a signal, a source configured to generate and send a voltage to each of the plurality of sensors, a microprocessor that receives signals from each of the sensors, calculates the circumference and volume of the body part, and communicates with a remote processing unit to identify and store trends in the body part over time. In that wearable device, the plurality of sensors may comprise a plurality of stretchable wires having electrical resistances that increase in linear proportion with length. In the wearable device, the output received from each of the sensors indicates a resistance across each sensor. In that wearable device, a push button may power the system on and a Bluetooth™ connection to transmit the output from each of the sensors. In that wearable device, the wearable device may be a brace configured to be worn on a human leg and foot. In that wearable device, the brace may be configured to measure the volume of a lower segment of the human leg and wherein the microprocessor comprises a microcontroller configured to calculate the leg volume based on the circumference measured at each sensor and a predefined leg model.

The plurality of sensors may comprise three stretchable wires attachable to a lower leg portion of a sock and forming an annular ring around a circumference of the lower leg portion of a sock. The wearable device may be a brace and may further include a wire that intersects itself configured for placement at an upper foot surface.

A system for measuring changes in volume of a body part of a user may comprise a wearable device as discussed above; a transmitter configured to transmit signals generated by the plurality of sensors; and a remote processing unit configured to receive the output from the microprocessor, and identify and store trends in the human leg volume over time.

A system for measuring changes in volume of a body part of a user, the system may comprise a wearable device as disclosed above, a transmitter configured to transmit signals generated by the plurality of sensors; and a processor configured to receive the signals, process the signals to determine a circumference at each of the plurality of sensors, calculate a volume of the body part based on the determined circumferences, and compare the determined volume of the body part with at least a previously determined volume to identify a change in volume of the body part. The system may further include a memory coupled to the processor, wherein the processor is configured store the determined volume and changes in volume over time in the memory. The processor may be configured to compare the determined volume with previously determined volumes and identify presence or severity of edema in the body part. The processor may also be configured to identify presence or severity of edema by comparing the identified change in volumes with a predetermined diagnostic edema baseline. The processor may further be configured to determine the efficacy of a therapy or treatment based on the identified change in volumes.

The plurality of sensors included in the system may include three sensors mounted on a brace positionable such that the three sensors surround a circumference of a lower human leg; and a sensor mounted on the brace positioned such that the sensor is configured to be in contact with a top surface of a human foot. The three sensors may measure the volume of a lower segment of the human leg and the intersecting sensor on a top surface of the human foot may measure the volume at an ankle of the human leg.

A method for measuring changes in volume of a body part of a user may comprise providing a wearable device comprising a plurality of sensors and a microprocessor for the user to wear on the body part receiving signals generated by the plurality of sensors; and processing the received signals by a processor to determine a circumference at each of the plurality of sensors, calculate a volume of the body part based on the determined circumferences, and compare the determined volume of the body part with at least a previously determined volume to identify a change in volume of the body part. In the method, the wearable device may be configured to be worn on a human leg and foot, in particular the method comprising measuring the volume of a lower segment of the human leg. The plurality of sensors may comprise a plurality stretchable of resistor wires.

The method may further include measuring a resistance across each sensor, wherein the signal generated by each of the sensors indicates said resistance. The method may further include storing the determined volume and changes in volume over time in a memory coupled to the processor.

The plurality of sensors used in the method may include three sensors mounted on a brace positioned such that the three sensors surround a circumference of a lower human leg; and a sensor mounted on the brace positioned such that the sensor is configured to be in contact with a top surface of a human foot. The three sensors may measure the volume of a lower segment of the human leg and an intersecting sensor may measure the volume at an ankle of the human leg. The wearable device may be configured to transmit the determined volume to a remote processor to compare the determined volume with previously determined volumes.

Although certain embodiments have been described and illustrated in exemplary forms with a certain degree of particularity, it is noted that the description and illustrations have been made by way of example only. Numerous changes in the details of construction, combination, and arrangement of parts and operations may be made. Accordingly, such changes are intended to be included within the scope of the disclosure, the protected scope of which is defined by the claims.

The invention claimed is:

1. A brace for measuring changes in human leg volume comprising:
   a plurality of sensors that each output a signal;
   a source configured to generate and send a voltage to each of the plurality of sensors; and
   a microprocessor that receives the signals from each of the sensors, calculates a human leg circumference and human leg volume based on the received signals, and communicates with a remote processing unit; and
   the remote processing unit configured to receive a communication of the human leg circumference and human leg volume from the microprocessor, and identify and store trends in the human leg volume over time,
   wherein the brace further includes a further sensor in the form of a wire that intersects itself positioned on the brace and the intersection on the brace configured for placement at an upper foot surface,
   wherein the microprocessor is configured to calculate the human leg volume based on a predefined leg model.

2. The brace of claim 1, wherein the plurality of sensors comprise a plurality of stretchable wires having electrical resistances that increase in linear proportion with length.

3. The brace of claim 1, wherein the signals received from each of the sensors indicates a resistance across each sensor.

4. The brace of claim 1, wherein the brace includes a push button to power the brace on and a wireless connection to transmit the signals from each of the sensors.

5. The brace of claim 1, wherein the remote processing unit is configured to compare the calculated human leg volume with a previously determined calculated leg volume to determine a presence or severity of edema.

6. The brace of claim 1, wherein the plurality of sensors comprise three stretchable wires attached to a lower leg portion of a sock and forming an annular ring around a circumference of the lower leg portion of the sock.

7. A system for identifying change in volume of a body part of a user, the system comprising:
   a wearable device comprising a plurality of sensors;
   a transmitter configured to transmit signals generated by the plurality of sensors; and
   a processor configured to receive the signals, process the signals to determine a circumference at each of the plurality of sensors, calculate a volume of the body part based on the determined circumferences, and compare the calculated volume of the body part with at least a previously determined volume to identify the change in volume of the body part,
   wherein the plurality of sensors include: three sensors mounted on a brace positioned such that the three sensors on the brace are configured to surround a circumference of a lower human leg; and a sensor mounted on the brace positioned such that the sensor intersects itself on the brace and the intersection is configured to be in contact with a top surface of a human foot,
   wherein the processor is configured to calculate the volume of the body part based on a predefined leg model.

8. The system of claim 7, wherein the wearable device is configured to be worn on the lower human leg and foot.

9. The system of claim 8, wherein the volume of the body part comprises a volume of a lower segment of the lower human leg.

10. The system of claim 7, wherein the plurality of sensors are a plurality of stretchable resistor wires.

11. The system of claim 7, wherein the signal generated by each of the sensors indicates a resistance measured across each sensor.

12. The system of claim 7, further including a memory coupled to the processor, wherein the processor is configured store the calculated volume of the body part and a plurality of identified changes in volume of the body part over time in the memory.

13. The system of claim 7, wherein the volume of the body part comprises volumes of the lower human leg and the ankle, wherein the three sensors measure the volume of the lower human leg and the sensor configured to contact the top surface of the human foot measures the volume at the ankle.

14. The system of claim 7, wherein the processor is configured to compare the calculated volume of the body part with at least the previously determined volume of the body part and identify a presence or severity of edema in the body part.

15. The system of claim 7, wherein the processor is configured to identify a presence or severity of edema by comparing the identified change in volume of the body part with a predetermined diagnostic edema baseline.

16. The system of claim 7, wherein the processor is configured to determine an efficacy of a therapy or treatment based on the identified change in volume.

17. A method for measuring change in volume of a body part of a user, the method comprising:
   providing a wearable device comprising a plurality of sensors and a microprocessor for the user to wear on the body part;
   receiving signals generated by the plurality of sensors; and
   processing the received signals by the microprocessor to determine a circumference at each of the plurality of sensors, calculate a volume of the body part based on the determined circumferences, and compare the calculated volume of the body part with at least a previously determined volume of the body part to measure the change in volume of the body part, wherein the plurality of sensors include:

three sensors mounted on a brace positioned such that the three sensors surround a circumference of a lower human leg; and a sensor mounted on the brace positioned such that the sensor intersects itself on the brace and is configured to be in contact with a top surface of a human foot, wherein the microprocessor is configured to calculate the volume of the body part based on a predefined leg model.

18. The method of claim 17, wherein the wearable device is configured to be worn on the lower human leg and foot.

19. The method of claim 18, wherein the body part is the lower human leg.

20. The method of claim 17, wherein the plurality of sensors comprise a plurality of stretchable of resistor wires.

21. The method of claim 17, wherein the signal generated by each of the sensors indicates a resistance measured across each sensor.

22. The method of claim 17, further including a memory coupled to the microprocessor, wherein the microprocessor is configured store the calculated volume of the body part and changes in the calculated volume of the body part over time in the memory.

23. The method of claim 17, wherein the volume of the body part comprises volumes of the lower human leg and the ankle, wherein the three sensors measure the circumference of the lower human leg and the sensor mounted on the brace configured to be in contact with the top surface of the human foot is an intersecting sensor configured measure the volume at the ankle.

24. The method of claim 17, wherein the wearable device is configured to transmit the calculated volume of the body part to a remote processor to compare the calculated volume with stored previously calculated volumes of the body part and identify a presence or severity of edema in the body part.

25. The method of claim 24, wherein the remote processor is configured to determine an efficacy of a therapy or treatment based on subsequent measured changes in volumes.

* * * * *